United States Patent
Weffers-Albu et al.

(10) Patent No.: US 10,777,323 B2
(45) Date of Patent: Sep. 15, 2020

(54) DEVICE, SYSTEM AND METHOD FOR ASSESSING THE ABILITY OF A PERSON TO CARRY OUT ONE OR MORE ACTIVITIES

(71) Applicant: KONINKLIJKE PHILIPS N.V., Eindhoven (NL)

(72) Inventors: Mirela Alina Weffers-Albu, Boukoul (NL); Lukas Stefan Gorzelniak, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 468 days.

(21) Appl. No.: 15/535,728

(22) PCT Filed: Dec. 16, 2015

(86) PCT No.: PCT/EP2015/079910
§ 371 (c)(1),
(2) Date: Jun. 14, 2017

(87) PCT Pub. No.: WO2016/096935
PCT Pub. Date: Jun. 23, 2016

(65) Prior Publication Data
US 2017/0332948 A1   Nov. 23, 2017

(30) Foreign Application Priority Data

Dec. 19, 2014 (EP) .................... 14199416

(51) Int. Cl.
*G16H 50/30* (2018.01)
*A61B 5/11* (2006.01)
(Continued)

(52) U.S. Cl.
CPC .......... *G16H 50/30* (2018.01); *A61B 5/0496* (2013.01); *A61B 5/1113* (2013.01);
(Continued)

(58) Field of Classification Search
CPC ..................................................... A61B 5/16
See application file for complete search history.

(56) References Cited

U.S. PATENT DOCUMENTS

2004/0147817 A1  7/2004 Dewing et al.
2005/0113721 A1  5/2005 Reed et al.
(Continued)

OTHER PUBLICATIONS

Se Lawton et al. "Assessment of Older People: Self Maintaining and Instrumental Activities of Daily Living", The 5 Gerontologist 1969; 9: 179-86.
(Continued)

*Primary Examiner* — Carrie R Dorna

(57) ABSTRACT

The present invention relates to a device for assessing the ability of a person to carry out one or more activities, comprising an input unit for receiving physiological and/or behavioural data of the person, the physiological and/or behavioural data being related to one or more first level activities, a determination unit for determining a performance grade of the person regarding each first level activity based on the received physiological and/or behavioural data, and an assessment unit configured to assess an ability grade of the person to carry out one or more second level activities based on the determined performance grade, wherein each second level activity relates to one or more associated first level activities, wherein the assessment unit is further configured to output information indicative of the assessed ability grade.

17 Claims, 1 Drawing Sheet

(51) Int. Cl.
*A61B 5/0496* (2006.01)
*G06F 19/00* (2018.01)
*A61B 5/00* (2006.01)

(52) U.S. Cl.
CPC .......... *A61B 5/1123* (2013.01); *A61B 5/1124* (2013.01); *G06F 19/00* (2013.01); *G06F 19/3481* (2013.01); *A61B 5/0002* (2013.01); *A61B 5/486* (2013.01); *A61B 2503/08* (2013.01); *A61B 2505/07* (2013.01); *A61B 2562/0219* (2013.01); *A61B 2562/0247* (2013.01)

(56) References Cited

U.S. PATENT DOCUMENTS

2005/0234310 A1   10/2005   Alwan et al.
2012/0108909 A1   5/2012    Slobounov et al.
2012/0115682 A1   5/2012    Homsi
2014/0066802 A1   3/2014    Kaula et al.
2014/0163426 A1   6/2014    Alberts et al.

OTHER PUBLICATIONS

Howell, Sandra C. "Assessing the function of the aging adult", The Gerontologist 8.1Part1 (1968): 60-62.

AgingCare.com, AgingCare, LLC, https://www.agingcare.com/Products, 2016.

Yangsheng Xu et al, "A Sensor-Integrated Shoe-Based Information Gathering Platform", Homepage of Advanced Robotics Lab, The Chinese University of Hong Kong, http://www.cuhksz-rimlab.org/node/337, 2014.

P.J. Antonio, "Quantifying stair gait stability in young and older adults, with modifications to insole hardness" Gait & Posture, vol. 40, Issue 3, Jul. 2014, pp. 429-434., DOI: 10.1016/j.gaitpost.2014.05.009.

Lee, Matthew L., "Task-Based embedded assessment of functional abilities for aging in place", Human-Computer Interaction Institute School of Computer Science, Carnegie Mellon University, Pittsburgh, Pennsylvania, USA 15213, Aug. 2012.

DEVICE, SYSTEM AND METHOD FOR ASSESSING THE ABILITY OF A PERSON TO CARRY OUT ONE OR MORE ACTIVITIES

CROSS-REFERENCE TO PRIOR APPLICATIONS

This application is the U.S. National Phase application under 35 U.S.C. § 371 of International Application No. PCT/EP2015/079910, filed on 16 Dec. 2015, which claims the benefit of European Patent Application No. 14199416.0, filed on 19 Dec. 2014. These applications are hereby incorporated by reference herein.

FIELD OF THE INVENTION

The present invention relates to a device, a system and a method for assessing the ability of a person to carry out one or more activities. In particular, the present invention discloses a device, system and method for automatic assessment of self-care ability of elderly patients. It finds applications in health care delivery in hospitals and at homes.

BACKGROUND OF THE INVENTION

Self-dependence and self-care activities of the elderly are essential for maintaining their state of health, well-being and quality of life. In this regard, systems and methods have been proposed for monitoring an assessment of ability/disability of patients or elderly persons that are cognitively unimpaired with a decreasing ability to perform self-care activities.

Such systems and methods are proposed to assess disability based on appointment by a profession who uses questionnaires and/or medical tests designed for that purpose. These assessments are, however, only punctual, rare and/or sporadic measurements of the patient's ability and thus cannot capture accurately the trends of self-care disability. Therefore, such system and methods lead often to a delay of support, as the moment when the patient starts needing supporting is not captured. Consequently, this causes increased risk of the occurrence of an adverse event or even an accident.

Moreover, the systems and methods known from the art focus on providing solutions starting from the premises that a deficiency in performing self-care activities has already been established. The disadvantage of this approach is that this usually becomes apparent and happens after the occurrence of an adverse event, such as after the patient has fallen in the bath tub.

US 2004/0147817 A1 discloses a system and method for assessing a functional or medical ability of an actor in an environment. The system is configured to retrieve data from a plurality of data sources and to automatically evaluate a functional or medical ability of the actor based upon information from the retrieved data. Furthermore, the system is configured to assign information from the data sources to baseline function categories.

Further systems and/or methods are known from Se Lawton et al. "Assessment of Older People: Self Maintaining and Instrumental Activities of Daily Living", The Gerontologist 1969; 9:179-86, and from Howell, Sandra C. "Assessing the function of the aging adult", The Gerontologist 8.1 Part 1 (1968): 60-62. Still further systems and/or methods are known from the website "http://www.aging-care.com/Products".

SUMMARY OF THE INVENTION

It is an object of the present invention to provide a device, system and method for assessing the ability of a person to carry out one or more activities, which enable to increase the accuracy of the self-care assessment. Another object of the present invention is the provision of a device, system and method which proactively assist the user to become aware of the need of the concerned person early in time, so as to prevent adverse events from occurring or to reduce the risk of the occurrence of adverse events.

In a first aspect of the present invention a device for assessing the ability of a person to carry out one or more activities is presented that comprises an input unit for receiving physiological and/or behavioural data of the person, the physiological and/or behavioural data being related to one or more first level activities, a determination unit for determining a performance grade of the person regarding each first level activity based on the received physiological and/or behavioural data, and an assessment unit configured to assess an ability grade of the person to carry out one or more second level activities based on the determined performance grade, wherein each second level activity relates to one or more associated first level activities. The assessment unit may be further configured to output information indicative of the assessed ability grade.

In a further aspect of the present invention a system for assessing the ability of a person to carry out one or more activities is presented that comprises a sensing unit for generating physiological and/or behavioural data and a device as claimed herein, the device being configured to receive the physiological and/or behavioural data from the sensing unit.

In a further aspect of the present invention a method for assessing the ability of a person to carry out one or more activities, comprising receiving physiological and/or behavioural data of the person, the physiological and/or behavioural data being related to one or more first level activities, determining a performance grade of the person regarding each first level activity based on the received physiological and/or behavioural data, assessing the ability grade of the person to carry out one or more second level activities based on the determined performance grade, wherein each second level activity relates to one or more associated first level activities. The method may include the step of outputting information indicative of the assessed ability grade.

Preferable embodiments of the invention are defined in the dependent claims. It shall be understood that the claimed system and method have similar and/or identical preferable embodiments as the claimed device and as defined in the dependent claims.

The input unit is configured to receive the physiological and/or behavioral data, wherein the received physiological and behavioral data are related to one or more first level activities. Preferably, the input unit is configured to receive such data from an external sensing unit for detecting one or more first level activities performed by the person and generating the physiological and/or behavioral data based on the detection.

The first level activities may include, without being limited to, walking, sitting up, standing, lifting an object, hearing, holding/carrying an object, seeing, reading and/or frailty such as energy frailty. Correspondingly, the physiological and/or behavioral data may include pressure sensor data, accelerometer data, connected sender/receiver data, electrooculography (EOG) sensor data, ultrasonic sensor data, audio sensor data and/or RFID sensor data.

Based on the received physiological and/or behavioral data, the determination unit is able to determine the performance grade which refers to how well the person has performed the one or more first level activities. In this way, the determination unit determines the performance grade by evaluating the physiological and/or behavioral data related to each first level activity individually. The original physiological and/or behavioral data are thus graded/scored so as to determine the performance grade.

Based on the determined performance grade, the assessment unit is able to conduct an assessment of the ability of the person to carry out one or more second level activities. Each second level activity relates to one or more associated first level activities, wherein the second level activities may include, without being limited to, bathing, answering the phone, responding to the door bell, making a laundry, shopping, preparing meals, eating, clothing, taking medication and/or doing exercises. The assessment unit may comprise one or more algorithms, such as computational algorithms, for the assessment of the ability grade based on the performance grade determined by the performance unit.

In particular, the one or more associated first level activities need to be performed in order that the second level activity relating to the associated first level activities may be carried out. Hence, each second level activity requires or involves its corresponding one or more associated first level activities. It is understood that the first level activities may be viewed as basic activities or low-level activities, whose performance is required for carrying out the second level activity, which can be viewed as a high-level activity with a higher complexity level compared to the basic activities.

Advantageously, the present invention enables an ability assessment with increased accuracy. In particular, in contrast to the system known in the past, the present invention enables to grade/score the received physiological and/or behavioural data so as to determine the performance grade for each first level activity. This also enables to predict the ability of the concerned person to carry out an associated second level activity with high reliability. Such predicted ability, at least partially reflected by the ability grade, may enable the user to better know his/her limitation, or to provide valuable feedback to formal and informal caregivers, such as doctor(s), nurse(s), care provider(s), family, friend(s). Additionally or alternatively, this ability grade may be provided to a monitoring device or any other device such that increase such device behavior is altered, for instance increase the granularity of data or frequency of monitoring time.

Further, based on the afore-mentioned predictive ability assessment, the present invention advantageously enables to proactively assist the user to become aware of the need of the concerned person early in time. In this way, the user, in particular caregivers/caretakers/doctors, are able to proactively prevent adverse events from occurring or at least to reduce the risk of such events by providing personalized services and appropriate support.

Consequently, the present invention is advantageous regarding cost reduction for hospitalizations and advanced treatments, leading to improvements in quality of life and reduced care costs for the concerned person at the same time.

The input unit, the determination unit and the assessment unit may be individual elements of separate controllers and/or processors, alternatively individual elements of a single controller and/or processor, alternatively comprised in a common element of a single controller and/or processor.

In a preferable embodiment, the performance grade corresponds to one scale or an interval covering one or more scales of a first scaling. In this way, the performance grade is determined with high quantitative accuracy. Preferably, the performance grade can be determined for different first level activities using the same first scaling. Advantageously, this overcomes the difference between units of the physiological and/or behavioral data for different first level activities. The ability assessment is thus facilitated and more efficient.

In another preferable embodiment, the assessment unit is configured to assess the ability grade for each of the second level activities according to a second scaling, the ability grade being one of a plurality of scales of the second scaling. In this way, the ability grade for the second level activities is assessed with high quantitative accuracy. Preferably, the ability grade for different second level activities may be assessed using the same second scaling, which advantageously further facilitates the ability assessment.

In another preferable embodiment, the ability grade regarding each second level activity is based on the performance grade regarding at least one associated first level activity. In particular, an individual second level activity may relate to only one associated first level activity. Alternatively, an individual second level activity may relate to a plurality of associated first level activities. This means that the assessment unit is able to assess the ability grade regarding a second level activity that has been fully or partially carried out. Advantageously, the ability assessment, in particular an ability assessment for predicting the ability of the concerned person to complete a second level activity in future, is highly accurate.

Preferably, the device is configured to detect defect sensors by analyzing a consistency level of the performance grades for the plurality of first level activities. In this way, erroneously determined performance grades due to defect sensors giving rise to wrong sensor data may be detected when inconsistency occurs between the performance grades for the plurality of first level activities. Advantageously, the ability assessment is more accurate and reliable.

In another preferable embodiment, the device further comprises a memory unit for storing the received physiological and/or behavioral data, the determined performance grade and/or the assessed ability grade. In this way, the physiological and/or behavioral data, the determined performance grade and/or the assessed ability grade can be secured and accessed for further usage. Advantageously, this increases the security and the usability of the afore-mentioned data, performance grade and/or ability grade.

In another preferable embodiment, the device further comprises a monitoring unit for monitoring the assessed ability grade over time, the monitoring unit being configured to generate a feedback signal when detecting an abnormal ability grade regarding one of the second level activities, the abnormal ability grade being higher or lower than a predefined ability grade. This enables to follow up the ability grade of the person and to be aware of the abnormal ability grade. Advantageously, this enables to call preventive measures into service early in time so that hospitalization costs and costs for further treatments and/or medication are reduced.

In another preferable embodiment, the monitoring unit is configured to generate the feedback signal when the abnormal ability grade has been detected for a predefined length of time. In this way, the monitoring unit is suitable to count the time length from the moment of detecting the abnormal ability onwards until the abnormal ability grade diminishes.

Advantageously, this enables to detect abnormal tendencies of the concerned person regarding carrying out second level activities with increased reliability. Preferably, the monitoring unit is configured to derive the percentage of time length, in which the abnormal ability grade is detected over a predefined time length, wherein the feedback signal is generated when the derived percentage is higher than the predefined percentage. Advantageously, this further increases the reliability of the detection of abnormal tendencies.

In another preferable embodiment, the abnormal ability grade is a median ability grade averaged over a predefined length of time. Advantageously, this enables to further increase the reliability of the detection of abnormal tendencies.

In another preferable embodiment, the device further comprises an identification unit for identifying one or more first level activities associated with the second level activity, for which the abnormal ability grade has been detected, wherein the performance grade regarding the identified one or more first level activities is higher or lower than a predefined performance grade. In this way, the present invention enables to identify the one or more first level activities relevant for the occurrence of the abnormal ability. Further, by retrieving the performance grade regarding the identified first level activities, the present invention enables to call preventive measures into service without the need of retrieving the original data related to the identified first level activities, or the need of accounting for other first level activities which are of no or low relevance for the detected abnormal ability grade. Advantageously, this significantly increases the timeliness of preventive measures, thereby reducing the risk of adverse events.

In another preferable embodiment, the identification unit is further configured to determine for an identified first level activity to second level activities commonly associated with the identified first level activity. In this way, the present invention enables to determine, upon detecting the abnormal ability grade for a second level activity, another second level activity correlated to the first one. Advantageously, this enables to predict the ability of the concerned person to carry out a second level activity, wherein monitoring of the latter second level activity is not necessary. This means that the predicted ability may refer to a second level activity in future.

In another preferable embodiment, the device further comprises a recommendation generation unit for generating recommendation information related to the one or more first level activities and/or the one or more second level activities. Advantageously, preventive measures can be proactively called into service so that the risk of adverse events can be effectively reduced.

In a preferable embodiment, the sensing unit comprises a plurality of sensors, in particular a wearable sensor, a sensor mountable to a household object such as furniture, and/or a stationary sensor. In this way, different types of sensors are used to detect the basic abilities of the person, wherein a large spectrum of different basic activities can be covered. Advantageously, this increases the accuracy and reliability of the ability assessment.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
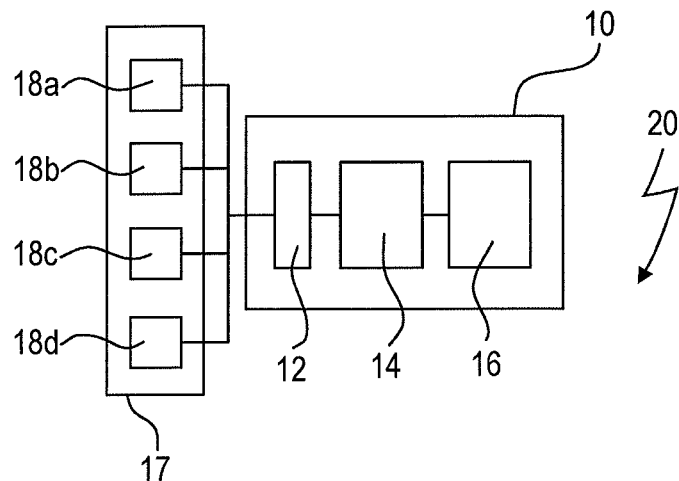
FIG. 1 shows a schematic block diagram of a device for ability assessment incorporated in a system.

FIG. 1 shows a schematic block diagram of a device 10 for assessing the ability of a person to carry out one or more activities. The device 10 comprises an input unit 12 for receiving physiological and/or behavioral data of the person, wherein the data are related to one or more first level activities. As can be seen in FIG. 1, the input unit 12 is configured to receive the physiological and/or behavioral data from a sensing unit 17 comprising a plurality of sensors 18a-d. It is understood that the sensing unit 17 is an external entity separate from the device 10.

The device 10 further comprises a determination unit 14 for determining a performance grade of the person regarding each first level activity based on the received physiological and/or behavioral data. The device 10 further comprises an assessment unit 16 for assessing the ability grade of the person to carry out one or more second level activities based on the determined performance grade, wherein each second level activity relates to one or more associated first level activities.

The device 10 and the sensing unit 17 are incorporated in a system 20 for ability assessment. The plurality of sensors 18a-d may comprise at least one pressure sensor, accelerometer, EOG sensor, ultrasonic sensor, audio sensor, connected sender and/or receiver, and RFID sensor, without being limited to the afore-mentioned sensor types. Preferably, the plurality of sensors 18a-d include at least a wearable sensor, a sensor mountable to the household object such as a furniture, garment, shoe, electronic products, etc., and/or a stationary sensor. The plurality of sensors 18a-d are preferably located in shoes, chairs, bed, bath tub, shopping bag, washing machine, glasses, tablet, television, the bracelet of a patient, etc. The plurality of sensors 18a-d are preferably embedded in the patient's home. Table 1 contains a list of exemplary sensors, the signal acquisitioned as well as the location where each sensor is embedded.

TABLE 1

| Sensors | Signal recorded | Sensor location |
| --- | --- | --- |
| Connected sensor & receiver | For each step: Time stamp, Foot identifier Foot position | Shoes |
| Pressure sensor | Pressure level | Shoes |
| Accelerometer | Acceleration | Chairs, Bed, Bath-tub, Shopping bag, Washing machine |

TABLE 1-continued

| Sensors | Signal recorded | Sensor location |
|---|---|---|
| EOG | EOG signal | Glasses |
| Ultrasonic sensor | Distance | Tablet |
| Audio sensor | Audio signal | TV |
| RFID | Patient ID | Patient bracelet (sender), Chairs (receiver), Bed (receiver), Bath-tub (receiver), Shopping bag (receiver) |

Using the plurality of sensors 18a-d, the one or more first level activities being low-level activities can be detected. Table 2 shows an exemplary list of low-level activities.

TABLE 2

| Low-level Activities |
|---|
| Walk |
| Sit up |
| Stand |
| Lift (xkg) |
| Hear |
| Holding/Carrying item |
| See/Vision |
| Read |
| General level of energy/frailty |

In this way, the performance grade of the person regarding each first level activity can be determined based on the received data. Consequently, the ability grade of the person to carry out one or more second level activities can be assessed based on the determined performance grade. Table 3 shows an exemplary list of second level activities being high-level activities.

TABLE 3

| High-level Activities |
|---|
| Bathing |
| Answer the door |
| Answer the phone |
| Laundry |
| Shopping |
| Prepare meals |
| Eating |
| Clothing |
| Take medication |
| Exercise |

Each high-level activity relates to one or more associated low-level activities, as shown in the following Table 4, which presents each of the high-level activities in Table 3 with corresponding associated low-level activities of Table 2. For instance, in order to carry out the high-level activity "answer door", the concerned person needs to perform the low-level activities "walk" and "hear bell".

TABLE 4

| High-level Activities | Low-level Activities |
|---|---|
| Bathing | Walk, Sit up, Stand up |
| Answer door | Walk Hear bell |
| Answer phone | Hear phone ring |
| Shopping | Walk Lift Vision |

TABLE 4-continued

| High-level Activities | Low-level Activities |
|---|---|
| Prepare meals | Walk Vision Hold |
| Eating | Sit up Hold |
| Clothing | Sit up, stand up |
| Take medication | See (Vision) Read Lift |
| Exercise | Walk Frailty level |
| Laundry | Washing machine activity |

Frailty level is considered as a low-level activity in the scope of the present invention because it has bearing on the ability of a patient to exercise. "Washing machine activity" is also considered as a low-level activity in the scope of the present invention and it is the most practical way of determining if the patient is able to do laundry regularly. Table 5 shows the low-level activities listed in Table 2 with corresponding sensors, sensor location, signal processing and determination of performance grade. As can be seen in Table 5, the performance grade regarding each first level activity corresponds to one scale of a first scaling. For instance, for the first level activity "stand", the first scaling comprises two different scales being 0 and 1, wherein the scale 0 corresponds to the case where the person is not able to stand, wherein the scale 1 corresponds to the case where the person is able to stand. For the first level activity "sit up", the first scaling is the same as for "stand", wherein the two scales 0 and 1 correspond to the user not being able to sit up and being able to sit up, respectively.

The sensor data from only one sensor may be used to determine the performance grade regarding a first level activity. This is exemplarily shown for the first level activity "stand", wherein pressure level data are received for determining the performance grade. Here, only pressure sensors are used to detect changes in pressure level as the concerned person stands. Alternatively, sensor data from a plurality of sensors may be used to determine a performance grade regarding a first level activity. This is exemplarily shown for the first level activity "sit up". Here, pressure sensors to detect changes, in particular increase, in pressure level as the concerned person sits up. Further, accelerometers are used to detect significant increase in accelerometer signal amplitude. In addition, motion speed and/or learning values which are characteristic of sitting up for pressure level, accelerometer signal amplitude and/or speed may also be detected.

For different first level activities, different first scalings may be applied. For instance, the first scaling for the first level activity "walk" comprises five scales being 1-5 wherein the scale 1 corresponds to the case where the person is not able to walk, the scale 3 corresponds to the case where the person is able to walk but with difficulty, and the scale 5 corresponds to the case where the person has no difficulty to walk. Preferably, the user's grade of performing the first level activities increases with the scale. Further preferably, a scale of the first scaling for a first level activity may correspond to a specific value or a specific range of values of the physiological and/or behavioral data associated with that first level activity. The range of data values may be characterized by an upper threshold, a lower threshold or a median value.

TABLE 5

| Low-level Activity | Sensors | Sensor location | Signal processing performed | Performance Grade Determination |
|---|---|---|---|---|
| Stand | Pressure sensor | Shoes | Detect significant changes in pressure level at standing | Scale 0-1:<br>0 (not able to stand): Pressure level increase not sustained<br>Pressure level increase sustained |
| Sit up | Pressure sensors<br><br>Accelerometer | Bed Chairs | Detect significant increase in pressure level at sit up<br>Detect significant increase in accelerometer signal amplitude<br>Detect motion speed<br>Learning values characteristics of sitting up for pressure level, accelerometer signal amplitude and speed | Scale 0-1:<br>0 (not able to sit up: Pressure level increase not reaching values corresponding to sit up<br>Low Accelerometer activity<br>1 (able to sit up): Pressure level increase reaches values correspond-in to sit up<br>Pressure level increases sustained<br>Accelerometer activity characteristics of sitting-up<br>Motion speed characteristics to normal sit up |
| Walk | Connected sender & receiver<br>Pressure sensor | Shoes | Detect:<br>walking pattern<br>speed<br>gait parameters | Scale 1-5:<br>1 (not able to stand): Sit up or stand ability is 0<br>Walk speed is far lower than low limit value<br>3 (walk with difficulty): Irregular walk pattern (limps, numerous stops)<br>Average speed below normal speed values<br>5 (no difficult walking): regular walking pattern & speed within normal limit values |
| Lift | Accelerometer | Shopping bag | Detect significant increase in accelerometer signal amplitude<br>Detect motion speed | Scale 1-5:<br>1 (not able to lift): Insignificant Accelerometer activity and motion speed<br>3 (lift with difficulty): medium accelerometer activity detected<br>Low motion speed<br>5 (no difficulty lifting): Significant accelerometer activity detected<br>Motion speed characteristics to normal lifting |
| Hear | Connected sender & receiver<br>Pressure sensor<br>Audio sensor | Shoes<br>TV/radio | Detect user distance from TV/radio<br>Detect volume level of TV/radio | Scale 1-5:<br>1 (difficulty in hearing): Distance to TV < 5 m<br>Volume higher than threshold<br>3 (moderate hearing): Distance to TV < 5 m<br>Volume within normal limits, lower than median value of normal limits |

TABLE 5-continued

| Low-level Activity | Sensors | Sensor location | Signal processing performed | Performance Grade Determination |
|---|---|---|---|---|
| | | | | 5 (no difficulty hearing): Distance to TV < 5 m Volume within normal limits |
| Vision | EOG Ultrasonic sensor | Glasses Tablet | Vision test software that asks user to read a text which progressively becomes smaller Automatic reading detection from EOG signal As text becomes progressively smaller make text smaller software detects in the EOG signal how fast the reading progresses (reading speed) At the same time the system monitors the distance between the tablet and user Slower reading speed (increased reading stalls) and distance to tablet progressively deviating from normal limit values (as the user tries to accommodate for smaller print) are indicative of vision problems | Scale 1-5: 1 (poor eye sight): Distance to tablet outside normal bounds Slow reading speed, frequent stalls 3 (moderate eye sight): Distance to tablet outside normal bounds Moderate reading speed, incidental stalls 5 (good eye sight): Distance to tablet within normal bounds Normal reading speed, no stalls |
| Read | | | Questionnaires that: Asks user preferable language and determines language proficiency. Asks highest level of education achieved | Scale 1-5: 1 (difficulty in reading): Poor language proficiency Low educational level 3 (derate reading): Moderate language proficiency Low educational level 5 (no difficulty hearing): High language proficiency Moderate-high education level |

The weight implied regarding the low-level activity "lift" is the average of a grocery bag. The lifting activity required in this case is only that necessary to place the bag onto a transportation device (e.g. rollator, container, etc.)

Details of how automatic detection of standing, sitting up and walking is performed are descried in: Yangsheng Xu et al, "A SENSOR-INTEGRATED SHOE-BASED INFORMATION GATHERING PLATFORM", Homepage of Advanced Robotics Lab, The Chinese University of Hong Kong (http://www.google.de/imgres?imgurl=http://arl-.mae.cuhk. edu.hk/files/shoe.jpg&imgrefurl=http://arl-.mae.cuhk.edu.hk/zhhans/node/337&h=455&w=550&tbnid=drRWqfUcqC0aM:&zoom=1&docid=q1PrTR9b_T6ieM&ei=dSXGU62pM7CX0Q WegYHwBA&tbm=isch&iact=rc&uact=3&dur=2373&page=1&start=0&ndsp=29&ved=0C G0QrQMwFw); and P. J. Antonio, "Quantifying stair gait stability in young and older adults, with modifications to insole hardness", Gait & Posture, Volume 40, Issue 3, July 2014, Pages 429-434., DOI: 10.1016/j.gaitpost.2014.05.009, whose content is hereby incorporated by reference.

Table 6 shows the high-level activities listed in Table 3 with corresponding associated low-level activities and assessed ability grades.

TABLE 6

| High-level Activity | Low-level Activities | Ability Grade Assessment |
|---|---|---|
| Bathing | Walk Sit up Stand | Low (not able to bathe): Sit up ability: 0 Stand ability: 0 Walk ability: 1 |

TABLE 6-continued

| High-level Activity | Low-level Activities | Ability Grade Assessment |
|---|---|---|
| | | Moderate (able to bathe with difficulty): Sit up ability: 1 Stand ability: 1 Walk ability: ∈ (1, 3) High (able to bathe without difficulty): Sit up ability: 1 Stand ability: 1 Walk ability: >3 |
| Answer door | Walk Hear bell | Low: Hearing ability: 1 Walk ability: 1 Moderate: Hearing ability: ∈ (1, 3) Walk ability: ∈ (1, 3) High: Hearing ability: >3 Walk ability: >3 |
| Answer phone | Hear phone ring Walk | Low: Hearing ability: 1 Walk ability: 1 Moderate: Hearing ability: ∈ (1, 3) Walk ability: ∈ (1, 3) High: Hearing ability: >3 Walk ability: >3 |
| Shopping | Walk Lift | Low: Lift ability: 1 Walk ability: 1 Moderate: Lift ability: ∈ (1, 3) Walk ability: ∈ (1, 3) High: Lift ability: >3 Walk ability: >3 |
| Prepare meals | Walk Stand | Low: Stand ability: 0 Walk ability: 1 Moderate: Stand ability: 1 Walk ability: ∈ (1, 3) High: Stand ability: 1 Walk ability: >3 |
| Eating | Sit up Hold | Low: Sit up ability: 0 Walk ability: 1 High: Sit up ability: 1 |
| Clothing | Sit up stand | Low: Sit up ability: 0 Stand ability: 0 Moderate: Sit up ability: 1 Stand ability: 0 High: Sit up ability: 1 Stand ability: 1 |
| Take medication | See (Vision) Read Lift | Low: Eye-sight ability: 1 or Read ability: 1 or Lift ability: 1 Moderate: Eye-sight ability: ∈ (1, 3) Read ability: ∈ (1, 3) Lift ability: ∈ (1, 3) High: Eye-sight ability: >3 Read ability: >3 Lift ability: >3 |
| Exercise | Walk Frailty level | Low: Walk ability: 1 Frailty level: below normal threshold Moderate: Walk ability: ∈ (1, 3) Frailty level: equal to normal threshold |
| Laundry | Washing machine activity | High: Walk ability: >3 Frailty level: above normal threshold Low: Washing machine activity detected in longer than 3 weeks Moderate: Washing machine activity detected is irregular, on average every 2 weeks High: Washing machine activity detected is regular, every 1 week |

Preferably, the assessment unit 16 is configured to assess the ability grade for each of the high-level activities according to a second scaling, wherein the ability grade is one of a plurality of scales of the second scaling. As can be seen in Table 6, the second scaling comprises preferably three scales: "high", "moderate" and "low".

Preferably, the second scaling is the same for at least two different high-level activities. Preferably, the ability grade regarding each high-level activity is based on the performance grade regarding at least one associated low-level activity. As can be seen in Table 6, the ability grade for the high-level activity "answer door" may be one of the three scales "low", "moderate" and "high". Each of the three scales is based on the performance grade regarding the two associated low-level activities "walk" and "hear bell".

Preferably, the assessment of the ability grade for a high-level activity is based on threshold values of the performance grade regarding the associated low-level activities. Further preferably, the ability grade is assessed to be a certain scale of the second scaling, for instance "low" for the high-level activity "taking medication", when the performance grade for at least one of the associated low-level activities is equal to, higher than or lower than the threshold value. Alternatively, the ability grade for a high-level activity may be assessed to be a certain scale of the second scaling, when the performance grade for at least two or all of the associated low-level activities is equal to, higher and/or lower than the threshold value.

Preferably, the threshold values are not limited to fixed values but may include a specific range of values and/or relevant trends.

Figure 2:
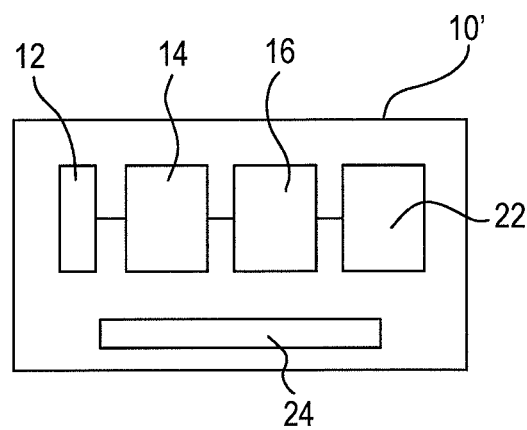
FIG. 2 shows a schematic block diagram of another device for ability assessment.

FIG. 2 shows a schematic block diagram of another device 10' for ability assessment, which comprises all components of the device 10 of FIG. 1. The device 10' further comprises a memory unit 24 for storing the received physiological and/or behavioral data, the determined performance grade and/or the assessed ability grade. The device 10' further comprises a monitoring unit 22 for monitoring the assessed ability grade over time, the monitoring unit 22 being configured to generate a feedback signal when detecting an abnormal ability grade regarding one of the second level activities, the abnormal ability grade being higher or lower than a predetermined ability grade. Preferably, the monitoring unit 22 is configured to generate the feedback signal when the abnormal ability has been detected for a predefined length of time. Further preferably, the abnormal ability grade is a median ability grade averaged over a predefined length of time. The predefined length of time may be set using the input unit 12.

Figure 3:
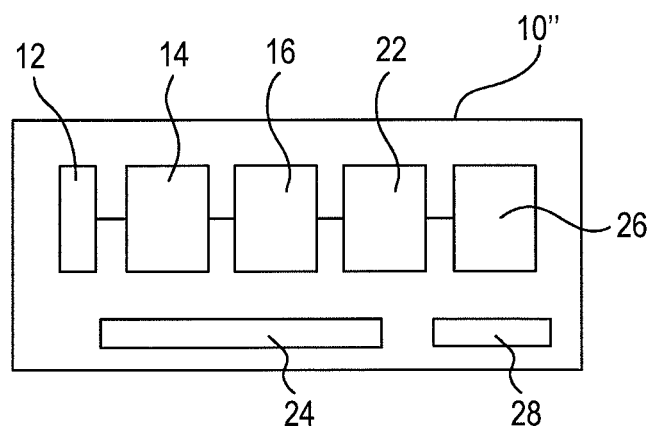
FIG. 3 shows a schematic block diagram of still a further device for ability assessment.

FIG. 3 shows a schematic block diagram of still a further device 10" for ability assessment, wherein the device 10" comprises all the components of the device 10' shown in FIG. 2 and additionally an identification unit 26. The identification unit 26 is configured to identify one or more first level activities associated with the second level activity, for which an abnormal ability grade has been detected, wherein the performed grade regarding the identified one or more first level activities is higher or lower than a predefined performance grade. Preferably, the identification unit 26 is further configured to determine for an identified first level activity to second level activities commonly associated with the identified first level activity. The device 10" further comprises a recommendation generation unit 28 for generating recommendation information related to the one or more first level activities and/or the one or more second level activities. In particular, the recommendation generation unit 28 is preferably configured to generate recommendation information to provide support regarding the first level activities associated with a second level activity showing abnormal ability grade. Further preferably, the recommendation generation is related to those first level activities associated with the second level activity showing abnormal ability grade, for which the performance grade has been determined to be higher or lower than a predefined performance grade.

It is understood that the device 10' and 10" shown in FIG. 2 and FIG. 3 may be incorporated into the system 20 in place of the device 10 shown in FIG. 1.

Figure 4:
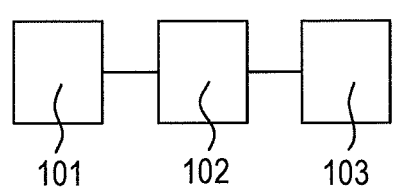
FIG. 4 shows a schematic block diagram of a method for ability assessment.

FIG. 4 shows a schematic block diagram of a method for ability assessment. In the step 101, physiological and/or behavioral data of the person are received, wherein the physiological and/or behavioral data are related to one or more first level activities. In step 102, a performance grade of the person regarding each first level activity is determined based on the received physiological and/or behavioral data. In step 103, an ability grade of the person to carry out one or more second level activities is assessed based on the determined performance grade, wherein each second level activity relates to one or more associated first level activities.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. A unit can be implemented in numerous ways, with software and/or hardware, to perform the various functions required. A processor is one example of a unit which employs one or more microprocessors that may be programmed using software (e.g., microcode) to perform the required functions. A unit may however be implemented with or without employing a processor, and also may be implemented as a combination of dedicated hardware to perform some functions and a processor (e.g., one or more programmed microprocessors and associated circuitry) to perform other functions.

Examples of unit components that may be employed in various embodiments of the present disclosure include, but are not limited to, conventional microprocessors, application specific integrated circuits (ASICs), and field-programmable gate arrays (FPGAs).

In various implementations, a processor or unit may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or unit or may be transportable, such that the one or more programs stored thereon can be loaded into a processor or unit.

Any reference signs in the claims should not be construed as limiting the scope.

The invention claimed is:

1. Device for assessing the ability of a cognitively unimpaired person to carry out one or more activities, comprising:
    an input unit for receiving data of a cognitively unimpaired person, the data including physiological data related to one or more first level activities;
    a determination unit for determining a performance grade of the person regarding each first level activity based on the physiological data; and
    an assessment unit configured to assess an ability grade of the person to carry out one or more second level activities based on the determined performance grade, wherein each second level activity is different from the one or more first level activities, and wherein each second level activity includes one or more associated first level activities.

2. Device of claim 1, wherein the performance grade corresponds to a scale or an interval covering one or more scales of a first scaling.

3. Device of claim 1, wherein the assessment unit is configured to assess the ability grade for each of the second level activities according to a second scaling, the ability grade being one of a plurality of scales of the second scaling.

4. Device of claim 3, wherein the ability grade regarding each second level activity is based on the performance grade regarding at least one associated first level activity.

5. Device of claim 1, further comprising a memory unit for storing the received physiological data, the determined performance grade, and the assessed ability grade.

6. Device of claim 1, further comprising a monitoring unit for monitoring the assessed ability grade over time, the monitoring unit being configured to generate a feedback signal when detecting an abnormal ability grade regarding one of the second level activities, the abnormal ability grade being higher or lower than a predefined ability grade.

7. Device of claim 6, wherein the monitoring unit is configured to generate the feedback signal when the abnormal ability grade has been detected for a predefined length of time.

8. Device of claim 6, wherein the abnormal ability grade is a median ability grade averaged over a predefined length of time.

9. Device of claim 6, further comprising an identification unit for identifying one or more first level activities associated with the second level activity, for which the abnormal ability grade has been detected, wherein the performance grade regarding the identified one or more first level activities is higher or lower than a predefined performance grade.

10. Device of claim 9, wherein the identification unit is further configured to determine for an identified first level activity two second level activities commonly associated with the identified first level activity.

11. Device of claim 1, further comprising a recommendation generation unit for generating recommendation information related to at least one of the one or more first level activities or the one or more second level activities.

12. A system for assessing the ability of a person to carry out one or more activities, comprising:
   a sensing unit configured to generate sensor data related to one or more first level activities performed by the person, the data including at least physiological data; and
   a device as claimed in claim 1, the device being configured to receive the physiological data associated with the person from the sensing unit.

13. System of claim 12, wherein the sensing unit comprises one or more sensors, the one or more sensors including at one or more of a wearable sensor, a sensor mountable to an object, or a stationary sensor.

14. The device of claim 1, comprising a sensing unit configured to generate sensor data related to the one or more first level activities performed by the person, the data including physiological data, wherein the sensing unit comprises one or more sensors, the one or more sensors including one or more of a wearable sensor, a sensor mountable to an object, or a stationary sensor.

15. The device of claim 14, wherein the one or more sensors comprise a wearable sensor.

16. Method for assessing the ability of a cognitively unimpaired person to carry out one or more activities, comprising:
   receiving data associated with a cognitively unimpaired person, the data including physiological data of the person, the data being related to one or more first level activities;
   determining a performance grade of the person regarding each first level activity based on the received physiological data; and
   assessing an ability grade of the person to carry out one or more second level activities based on the determined performance grade, wherein each second level activity is different from the one or more first level activities, wherein each second level activity includes one or more associated first level activities.

17. A non-transitory computer readable medium storing a computer program comprising program code means for causing a computer to carry out the steps of the method as claimed in claim 16 when said computer program is carried out on the computer.

* * * * *